United States Patent [19]
Fabian

[11] Patent Number: 5,057,095
[45] Date of Patent: Oct. 15, 1991

[54] SURGICAL IMPLEMENT DETECTOR UTILIZING A RESONANT MARKER

[76] Inventor: Carl E. Fabian, 577 NE. 96th St., Miami Shores, Fla. 33138

[21] Appl. No.: 437,182

[22] Filed: Nov. 16, 1989

[51] Int. Cl.$^5$ .............................................. A61F 13/16
[52] U.S. Cl. ................................... 604/362; 128/899; 604/20; 600/12; 600/13; 340/572
[58] Field of Search ................... 340/572, 573; 600/12, 600/13, 20; 604/362; 128/899

[56] References Cited

U.S. PATENT DOCUMENTS

| | | | |
|---|---|---|---|
| 3,587,583 | 6/1971 | Greenberg | 604/362 |
| 4,384,281 | 5/1983 | Cooper | 340/572 |
| 4,658,818 | 4/1987 | Miller Jr. et al. | 604/362 |
| 4,710,752 | 12/1987 | Cordery | 340/572 |
| 4,859,991 | 8/1989 | Watkins et al. | 340/572 |
| 4,872,018 | 10/1989 | Feltz et al. | 340/572 |

Primary Examiner—Francis Jaworski
Assistant Examiner—George Manuel
Attorney, Agent, or Firm—Ernest D. Buff

[57] ABSTRACT

Apparatus for detecting a surgical implement in human or animal tissue comprises a detector responsive to the presence, within an interrogation zone, of a surgical implement to which a marker is secured. The marker is adapted to produce identifying signal characteristics within a frequency band generated in the interrogation zone. Variations in the phase and or direction of the interrogating field and changes in the electromagnetic coupling between markers and receiver optimize coupling therebetween.

31 Claims, 12 Drawing Sheets

SURGICAL IMPLEMENT DETECTOR UTILIZING A RESONANT MARKER

BACKGROUND OF THE INVENTION

1. Field of the Invention

The present invention relates to a method for detecting a marked surgical implement such as a sponge, clamp, or catheter within a surgical wound in human or animal tissue irrespective of its position or orientation therewithin.

2. Description of the Prior Art

During the course of a surgical operation it is frequently necessary for articles, such as surgical sponges, gauzes, instruments, needles, and the like, to be placed into a wound cavity. Notwithstanding rigorous precautions attendant surgical procedures, such items are sometimes inadvertently lost during surgery and remain within the patient. When this happens, the patient can encounter serious consequences, including pain, infection, intestinal obstruction, and even death. The problem of retained surgical implements has existed since the earliest days of surgery. Procedures conventionally employed to prevent post-surgical implement retention include a manual search of the wound by the surgeon prior to closure and a careful accounting for all materials inserted and removed from the wound. The accounting function is customarily carried out by the operating room staff, usually the circulating nurse. Despite these precautionary measures the accidental retention of surgical implements continues to occur with disturbing regularity, even in prestigious institutions, and is regarded by surgeons as a major unsolved problem.

At present, manual search and physical count remain the primary methods used in detection of retained surgical implements. Most surgical instruments are composed of metal, and are easily detectable by x-ray. Sponges have been tagged with radiopaque markers to make them also visible on x-ray, but x-rays are not routinely done before completion of the operation because of several disadvantages including inconvenience, expense, loss of operative time, and radiation exposure. Postoperative x-rays suffer from some of the same disadvantages. Moreover, even when postoperative x-rays are taken, retained items are occasionally overlooked; but even if detected, require a second operation to effect their removal.

To overcome the difficulty of detecting retained surgical implements, it has been suggested that the implements be provided with a radioactive tracer. This technique, disclosed by U.S. Pat. No. 2,740,405 to Riordan, is subject to obvious hazards associated with use, storage and disposal of radioactive materials.

It has also been proposed that surgical sponges be marked with a flexible plastic impregnated with either paramagnetic or ferromagnetic materials in the form of powders. Detection of these marked sponges is accomplished by a metal detector. This method, taught by U.S. Pat. No. 3,422,816 to Robinson et al., provides very small signals difficult to detect over the width of a patient's body. In addition, the Robinson et al. technique provides no discrimination against other metal objects, such as staples which, though present within the surgical wound, are appointed for retention therewithin.

Yet another proposal, advanced by U.S. Pat. No. 3,587,583 to Greenberg, involves use of surgical sponges marked with magnetized particles whose presence is detectable with manetodiodes. In practice, however, the magnetic field generated by these particles is too small to be readily detected by the diodes.

U.S. Pat. No. 4,114,601 to Ables discloses the use of a small transponder fixed to a surgical sponge or instrument. This transponder exhibits gyromagnetic resonance at preselected frequencies. Detection is accomplished by nonlinear mixing of two frequencies impinging upon the transponder. The gyromagnetic resonance effect disclosed by Ables is a high frequency phenomenon, existing at frequencies of the order of about 5 gigahertz (5,000,000,000 cycles/sec). These frequencies, known as microwaves, are absorbed readily by animal tissue and are, in fact, used in microwave ovens for cooking. In use of the Ables type transponder, the energy developed goes primarily into heating tissue, rather than exciting the transponder into gyromagnetic resonance.

Other detection systems which have been proposed for use in making and detecting articles are, as presently practiced, not suitable for detection of retained surgical implements. One such detection system, disclosed by U.S. Pat. No. 4,510,489 to Anderson et al., finds utility in antitheft applications, as well as in such applications as access control, vehicle control, document control or product verification. The Anderson et al. apparatus operates by defining an interrogation zone of fixed dimensions. Articles having a marker affixed thereto pass through this zone. The passage of these articles through the zone is critical to certain detection of the marker since, in particular orientations, a stationary marker will not be detected within the zone. Detection of the marker in the Anderson et al. system is not assured unless the entire zone is traversed. For example, a marker having its long axis perpendicular to the floor will only be detected in the center of the zone, but not at the entry and exit points thereof; and a marker having its long axis parallel to the floor and parallel to the plane of the interrogating and receiving coils will be detected solely at entry and exit points and not in the center thereof.

Detection of an article tagged with a Anderson et al. type marker is not assured detection unless the article is moved through the entire zone. This is a matter of severe impracticality in applications where the article to be detected is a surgical instrument or sponge imbedded in a patient under surgery.

Thus, up to the present time, problems presented by post operative retention of surgical implements, though addressed by numerous workers in the art, have remained unsolved. Instead, the detection systems heretofore proposed have failed to account for marker orientation or they have utilized interrogating frequencies that are too high to prevent signal loss through their absorption in living tissue.

SUMMARY OF THE INVENTION

The present invention provides a method and apparatus for accurately and reliably detecting surgical implements within animal or human tissue.

The apparatus comprises a detector responsive to the presence, within an interrogation zone, of a surgical implement to which a marker is secured. The marker is adapted to produce identifying signal characteristics within the interrogation zone of the detector.

Briefly stated, the detector has means for defining an interrogation zone encompassing a surgical wound in human or animal tissue. An interrogation means is provided for generating within the interrogation zone an interrogating field having a frequency band below 1 gigahertz. A marker is secured to a surgical implement positioned within the wound. The marker comprises an element adapted to undergo resonance at a preselected frequency when excited by an interrogating field having at least one frequency component substantially equal to the preselected frequency or a harmonic thereof. The preselected frequency is chosen to be substantially equal to the resonance frequency of the marker element or a harmonic thereof. The interrogation means is also provided with a means for varying phase and/or direction of the interrogating field. A receiving means placed within the interrogation zone detects either the "ring-down", phase-shift, impedance or other identifying characteristic of the element in resonance, and indicates the same. The receiving means is further provided with means for changing, electromagnetic coupling with the marker to optimize coupling therebetween.

Advantageously, the method and apparatus of the invention detect retention of surgical implements with far greater accuracy than methods and means involving a physical count of implements that enter and exit the wound. The apparatus is inexpensive to construct, safer for the patient than postoperative X-rays and avoids risk to the environment posed by radioactive tracers. Generation of a strong signal is effected in a highly reliable manner. The signal is more easily distinguished than signals generated by magnetic detection systems, and is generated without the heating of tissue caused by microwave detection systems. Detection of marked implements is accomplished irrespective of marker position or orientation within the wound.

BRIEF DESCRIPTION OF THE DRAWINGS

The invention will be more fully understood and further advantages will become apparent when reference is made to the following detailed description of the preferred embodiment of the invention and the accompanying drawings in which.

DESCRIPTION OF THE PREFERRED EMBODIMENTS

Figure 1:
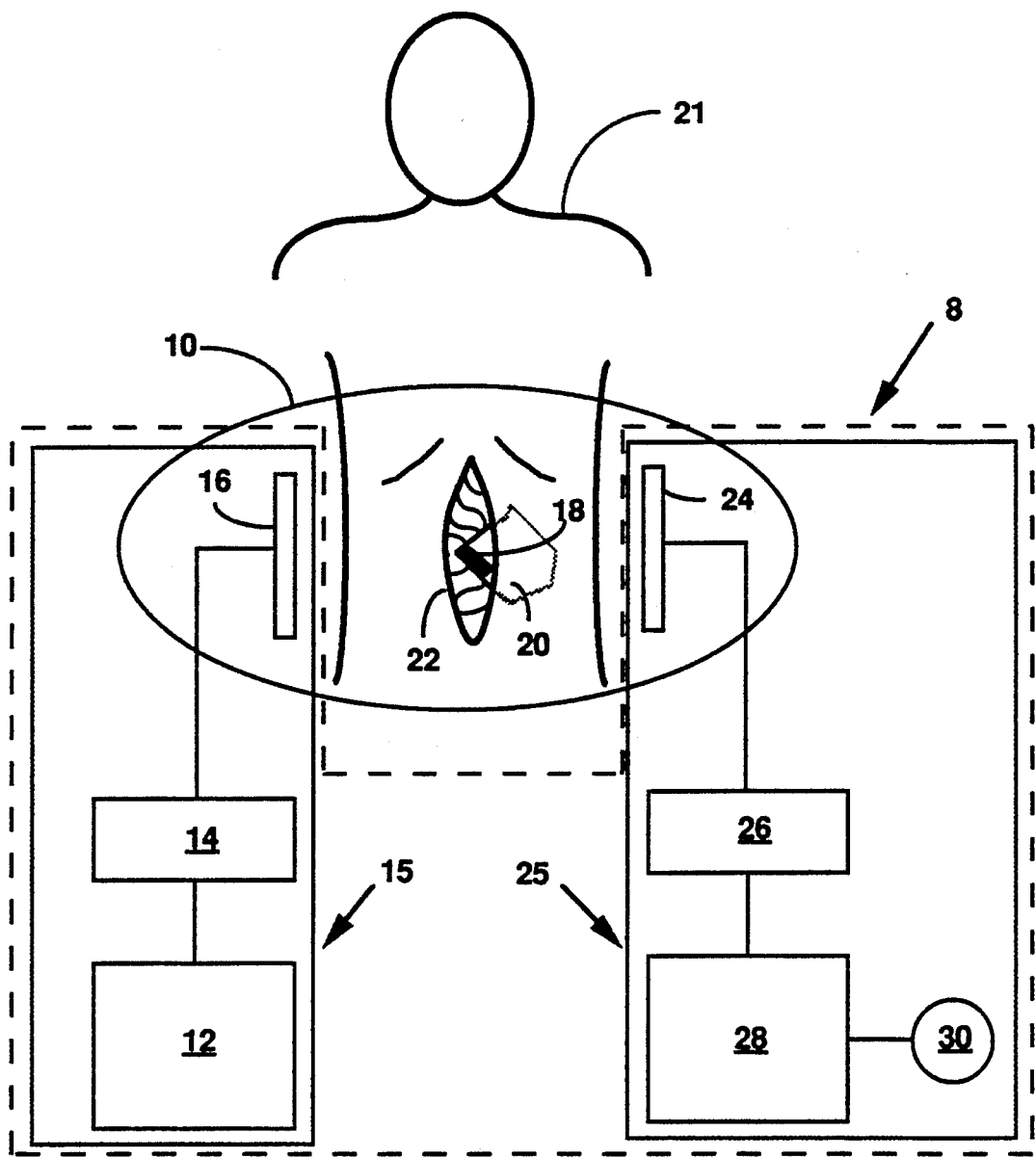
FIG. 1 is a block diagram of a surgical implement detector incorporating the present invention.

Referring to the drawings, there is shown in FIG. 1 a block diagram of a surgical implement detector 8 incorporating the present invention. A marker 18 is secured to a surgical implement 20, such as a sponge, positioned within the wound. The marker 18 is comprised of an element that is in resonance at a certain preselected frequency, within a range below about 1 gigahertz. The detector 8, comprised of an interrogating means 15 and a receiving means 25, defines a detection zone 10 encompassing a surgical wound 22 within patient 21.

Figure 2A:
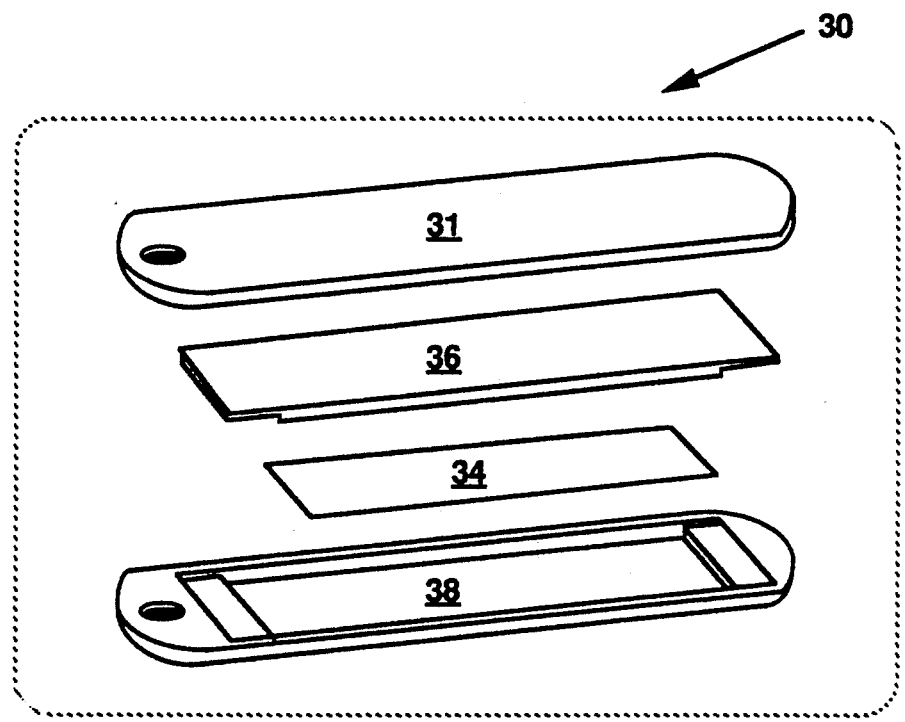
FIGS. 2a, 2b and 2c illustrate marker constructions for three types of resonant elements.
Figure 2B:
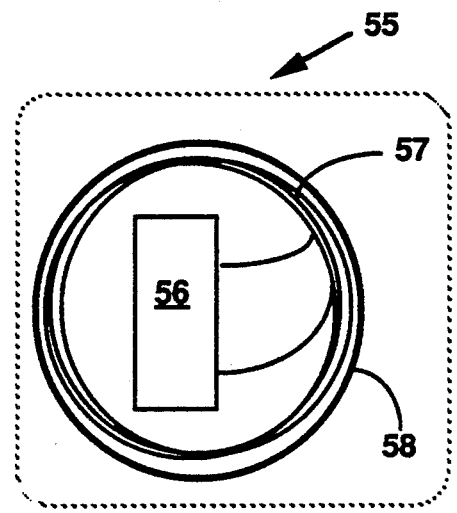
Figure 2C:
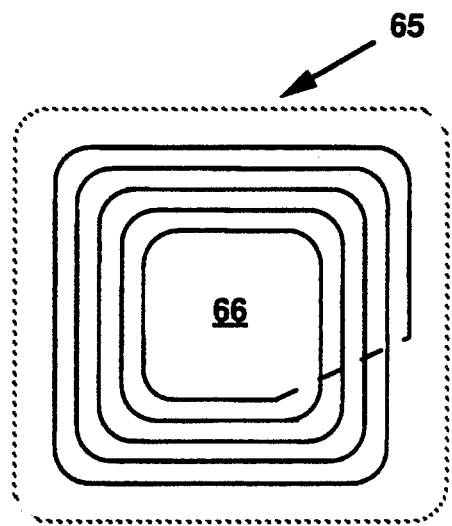

Within a range below about 1 gigahertz, resonance is of three types: magnetomechanical—in which case energy is alternatively stored in mechanical vibration and magnetic field, such as can be seen with a magnetostrictive amorphous ribbon; electromechanical—in which case energy is alternately stored in mechanical vibration and electric field, such as can be seen with a piezoelectric crystal; and electromagnetic—in which case energy is alternately stored in an inductor and a capacitor, such as can be seen with an LRC circuit. FIGS. 2a–2c depict marker constructions for each type of resonant element. The armed magnetomechanical marker 30 exhibits phase lag, with respect to the interrogating field generated by interrogator 15, below its resonant frequency and phase lead above its resonant frequency. Conversely, the electromagnetic marker 55 exhibits phase lead below and phase lag above its resonant frequency. Similarly, the resonant LRC marker 65 also shifts phase with frequency. At resonance none of the elements exhibit either phase lag or lead and are in phase with the interrogating field. When excited by the interrogator 15, each marker will generate a dipole field that exhibits a characteristic phase difference with the exciting field near resonance and a shift in phase as the exciting field's frequency traverses resonance. Since energy from the exciting field is being stored in these resonant elements, removal of this field will result in the gradual loss of the energy from the element, yielding a dipole field having a characteristic "ring-down" of energy.

The marker 30 is comprised of a strip of magnetostrictive, material adapted to be magnetically biased and thereby armed to resonate mechanically at a preselected frequency within the frequency band of the interrogation field. A hard ferromagnetic element 36 disposed adjacent to the strip 34 of magnetostrictive material is adapted, upon being magnetized, to arm the strip 34 to resonate at the preselected frequency. Case 38 and lid 31 are comprised of a material, such as ABS plastic, that will remain inert within the wound throughout the surgery. The strip 34 of magnetostrictive material has a magnetomechanical coupling factor, k, greater than zero, where $k^2 = 1 - (f_r/f_a)^2$, $f_r$ and $f_a$ being its resonant and antiresonant frequencies, respectively. The hard ferromagnetic element 36 is preferably a molded composite of a hard ferromagnetic powder, such as barium ferrite, and a plastic such as nylon or delrin. The concentration of magnetic powder to plastic is selected to supply a field substantially equal to the magnetic field required to obtain optimum magnetomechanical coupling in the magnetostrictive strip 34. For example, approximately 3 Oersteads of magnetic bias is required to obtain maximum magnetomechanical coupling in an unannealed amorphous alloy whose composition is substantially equal to $Fe_{40} Ni_{38} Mo_4 B_{18}$ in atomic weight percent. Alternatively, hard ferromagnetic element 36 is a thin strip of metal alloy such a vicalloy or Arnochrome. Upon exposure to the dc magnetic field, generated by the hard ferromagnet 36, or generated externally, the marker is characterized by a substantial change in its effective impedance as the applied ac field sweeps through the resonant frequency that provides the marker with signal identity. This signal identity is characterized by phase lead/lag described above. When the ac field is removed, the magnetostrictive strip 34 exhibits the longest mechanical ring-down at the resonant frequency. The preselected frequency is chosen to be substantially equal to the mechanical resonant frequency of the magnetostrictive strip or a harmonic thereof.

Alternatively, the marker 55 is comprised of a piezoelectric crystal 56, such as quartz. An air-core coil 57, occupying the inside diameter of case 58, is terminated across crystal 56 and is inductively coupled to the exciting field. Alternatively, an iron or ferrite core inductor is used in place of the coil 57. The marker 55 is characterized by a substantial change in its effective impedance as the applied ac field sweeps through the resonant frequency providing the marker with signal identity. This signal identity is characterized by phase lag/lead described above. When the ac field is removed, the crystal 56 exhibits the longest mechanical ring-down at the resonant frequency. The preselected frequency is chosen to be substantially equal to the mechanical resonant frequency of the piezoelectric crystal or a harmonic thereof.

As a further alternative, marker 65 is comprised of an inductor, a resistor, and a capacitor in a series LRC circuit, or alternatively a parallel LRC circuit. Or, the LRC circuit is comprised of printed circuit coil 66. The marker is characterized by a substantial change in its effective impedance as the interrogating field sweeps through the resonant frequency providing the marker 65 with signal identity. This signal identity is characterized by phase lag/lead described above. When the ac field is removed, the circuit exhibits the longest electrical ring-down at the resonant frequency. The preselected frequency is chosen to be substantially equal to the electrical resonant frequency of the LRC circuit or a harmonic thereof.

Referring again to FIG. 1, frequency generating means 12 generates a frequency encompassing the resonant frequency of marker 18 and supplies the power signal to the field generating means 16. A field changing means 14 varies the amplitude and direction of the magnetic field to alter the electromagnetic dipole coupling between the marker 18 and the magnetic field provided by the field generating means 16. A detecting means 28 having detecting antenna 24 detects either this resonance (i.e. ring-down) or the change in impedance (phase change) at the preselected resonant frequency. The detecting means 28 includes an antenna changing means 26 for changing the orientation and position of the detecting antenna 24 relative to the marker 18 to alter the electromagnetic dipole coupling therebetween. Below 10MHz, generating means 16 and detecting antenna 24 are both typically comprised of one or more coils. Above 10MHz, generating means 16 and detecting antenna 24 are both typically comprised of one or more monopole antennas or, alternatively, dipole antennas.

The signal detected at the detecting antenna by the aforesaid marker 18 is a product of the efficiency of energy transfer or coupling between the generating antenna 12 and the marker 18, and the efficiency of energy transfer or coupling between marker 18 and detecting antenna 24.

Figure 3:
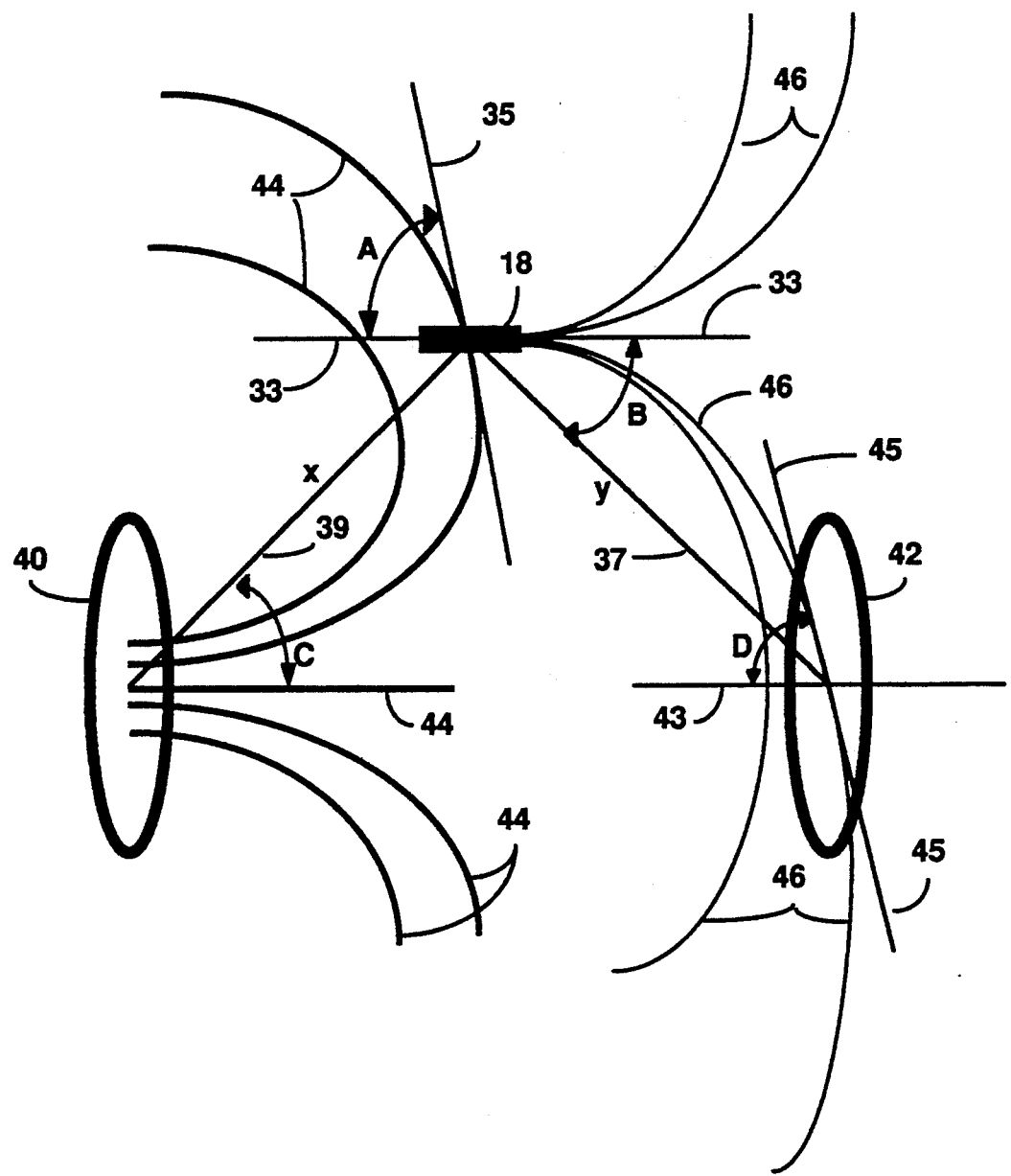
FIG. 3 is a diagrammatic representation of a marker and its dipole coupling with the field generating means and the detection antenna.

Referring to FIG. 3, the magnetic field generated by transmit coil 40 at the marker 18 location is a function of the angle and distance from the center of the coil 40 to the geometric center of the marker 18. The field at the marker location generated by transmit coil 40 is therefore a function of the angle C, and distance X represented by 39 in FIG. 3. In symbolic form: H=f (X,C).

The marker, being a dipole, forces another angular dependence on its coupling with the transmitted field, such that the field experienced by the marker 18 along its length is a function of A, where the angle A is subtended by the marker dipole axis 33 and the tangent 35 of the local magnetic flux line 44 generated by transmit coil 40. Therefore, the transmit coil 40 to marker 18 coupling is a function of the distance X and the two angles A and C, or $f_T(X,A,C)$. Similarly, when excited, the marker 18 generates a dipole field which, at the receiving coil 42, is a function of the distance Y, represented by 37 in FIG. 3, and the angle B. The angle B is subtended by the marker dipole axis 33 and the marker to receiving coil line 37. The receiving coil 42 is a dipole and couples with the marker's flux line 46 with an angular dependence D. The angle D is the angle between the receiving coil dipole axis 43 and the tangent 45 to the local flux lines 46 generated by the marker 18. Therefore, the marker to receiving coil signal coupling is a function of the distance Y between the two and the two angles B and D, or $f_R(Y,B,D)$. Typically, the signal voltage generated at receiving coil 42 by marker 18 excited by transmit coil 40 is: $V=wf_T(X,A,C)f_R(Y,B,D)$, where w is the resonance frequency.

The two coupling functions $f_T(X,A,C)$ and $f_R(Y,B,D)$ describe the significant difficulty encountered in the detection of stationary markers using a fixed receive and transmit antenna. Maximum coupling, and therefore maximum signal voltage at the receiver coil 42, occurs when each of three dipoles presented by the marker 18, the transmitting coil 40 and the receiving coil 42 are parallel and share the same major axis, i.e. when A,B,C, and D are each equal to zero. The coupling, and therefore the signal voltage, approaches zero when the angles approach 90 degrees.

Figure 4A:
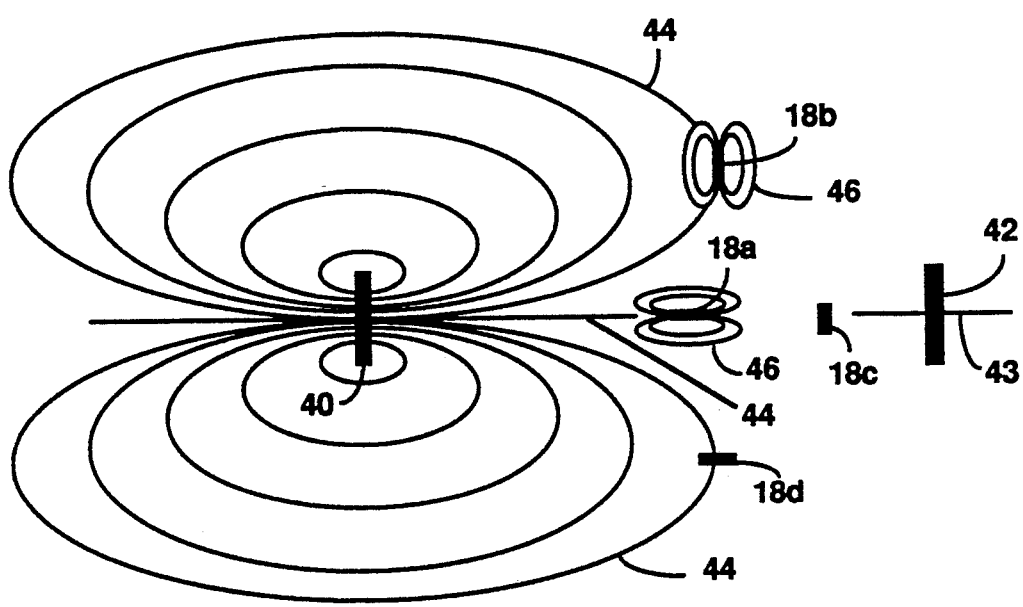
FIGS. 4a and 4b are diagrammatic overhead representations of markers at different orientations with respect to the field generating means and the detection antenna.
Figure 4B:
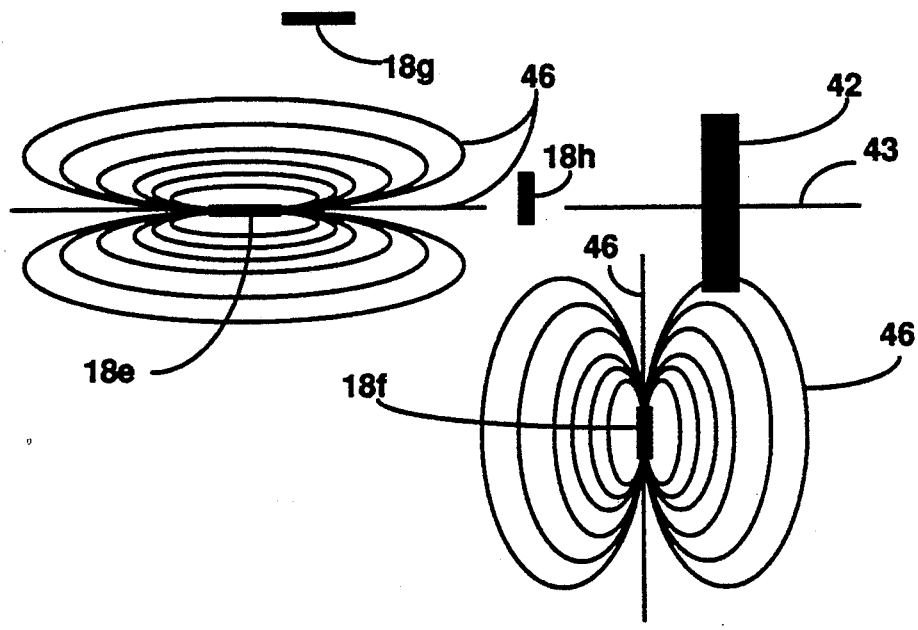

This phenomena is due to the fact that, for a given distance between two dipoles, strong coupling is achieved when the axis of the receiving dipole is parallel to the field lines of the transmitting dipole. Conversely, weak coupling is achieved when the axis of the receiving dipole is perpendicular to the field lines of the transmitting dipole. FIGS. 4a and 4b illustrate this point. Transmit coil 40 being a dipole, generates a magnetic field as depicted in FIG. 4a. Magnetic field flux lines 44 emanate from the face of the transmit coil and return symmetrically through the rear face of the coil. Marker 18a will receive maximum excitation since angles A and C are zero. Marker 18b will be strongly excited but not to the level of marker 18a since, with marker 18b, C does not equal zero and its distance X to the coil 40 is greater than the distance experienced by marker 18a. Markers 18c and 18d receive little if any excitation since their dipole lengths are perpendicular to the local magnetic flux lines. As stated above, this transmit coil to marker coupling can be mathematically represented as $f_T(X,A,C)$.

Similarly, the marker to receiver coil coupling is illustrated in FIG. 4b. Marker 18e generates the strongest signal in coil 42 with marker 18f generating the next strongest signal. Markers 18g and 18h both couple very poorly with receiver coil 42 and therefore generate little if any signal. The coupling between receiver coil 42 and each of markers 18g and 18h is represented mathematically as $f_R(Y,B,D)$.

Figure 5:
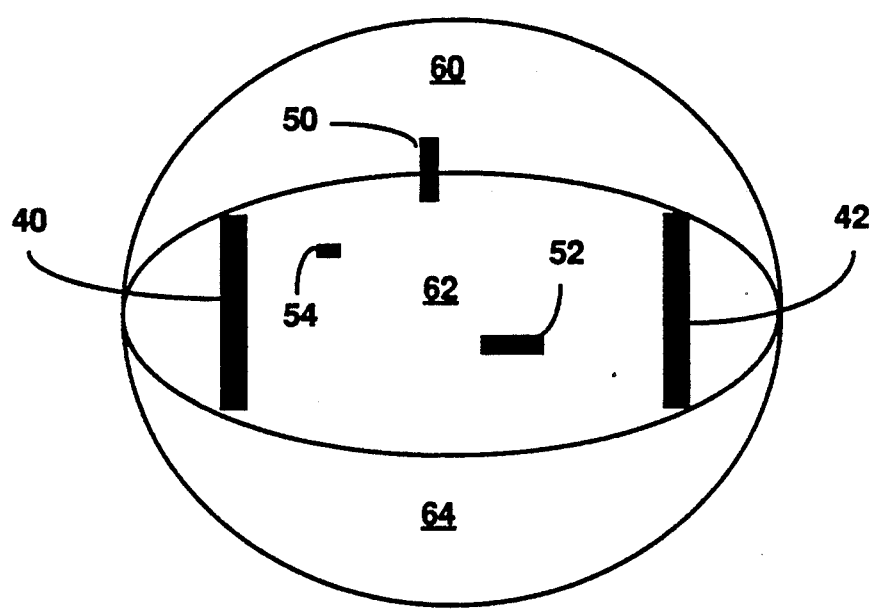
FIG. 5 is a diagrammatic overhead representation of three areas within the interrogation zone having different responses to maker orientation.

Resultant system coupling, the product of $f_T(X,A,C)$ and $f_R(Y,B,D)$, is illustrated by an overhead view of the detector in FIG. 5 wherein there are defined 3 marker orientations. In the parallel orientation 50, the marker length is parallel to the plane of the coils 40 and 42. The perpendicular orientation 52 exists when the marker length is perpendicular to the plane of the coils 40 and 42. A vertical orientation 54 is presented when the marker length is perpendicular to orientations 52 and 54. Referring to FIG. 5, the perpendicular orientation 52 of the marker 18 generates a strong signal in zone 62 and a weak signal in zones 60 and 64. The parallel orientation 50 of the marker 18 generates a strong signal in zones 60 and 64, and a weak signal in zone 62. In the vertical orientation 54, the marker 18 generates little or no signal in zone 62 and no significant signal in zones 60 and 64.

The orientation sensitivity of marker 18 has not posed a problem in use of magnetomechanical systems employed for purposes of antitheft, access control or sorting. In these systems, the marker is attached to an article or person moving through the interrogation zone, and is thereby caused to move into strong signal zones. Such movement of the marker 18 within the zone of interrogation 10 is highly impractical when the marker 18 is used in detection of a surgical implement 20 imbedded within the surgical wound 22 of a patient 21. On the other hand, for the reasons set forth previously, the necessity for achieving the highest degree of accuracy in detection of such surgical implements 20 is readily apparent.

Figure 6A:
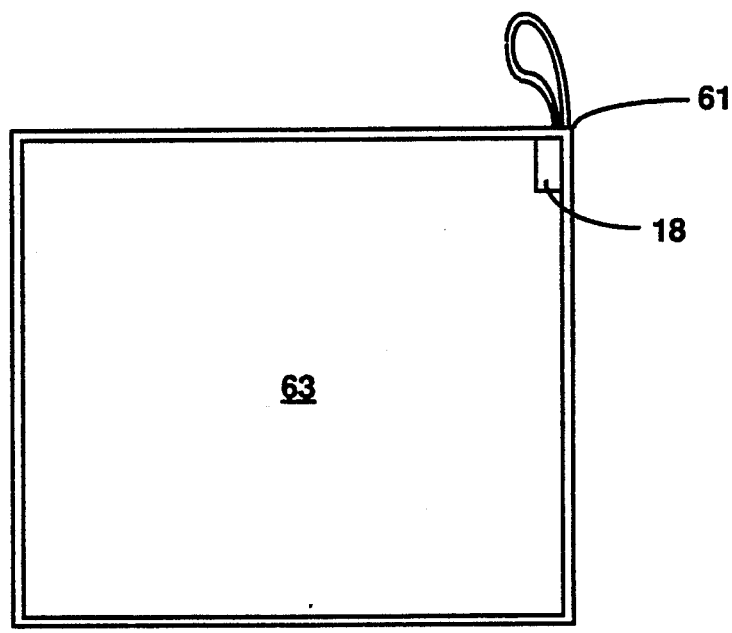
FIGS. 6a and 6b illustrate a marker attached to two different surgical implements.
Figure 6B:
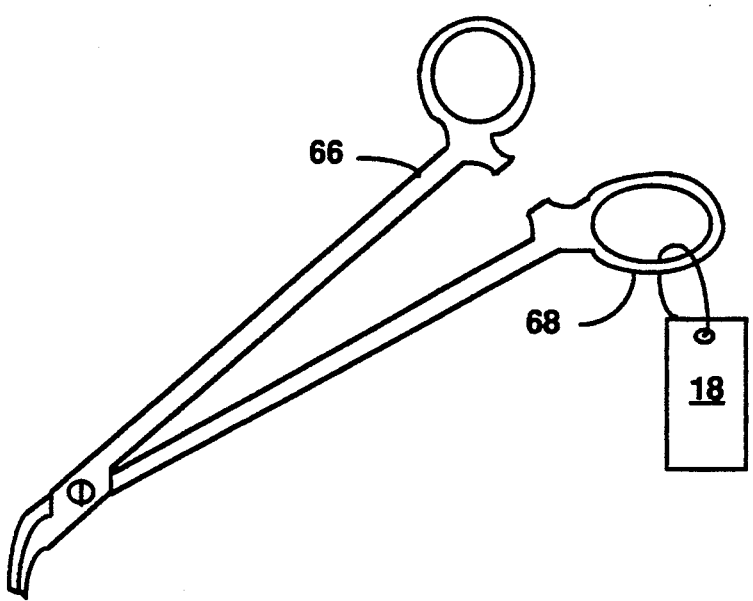
Figure 7A:
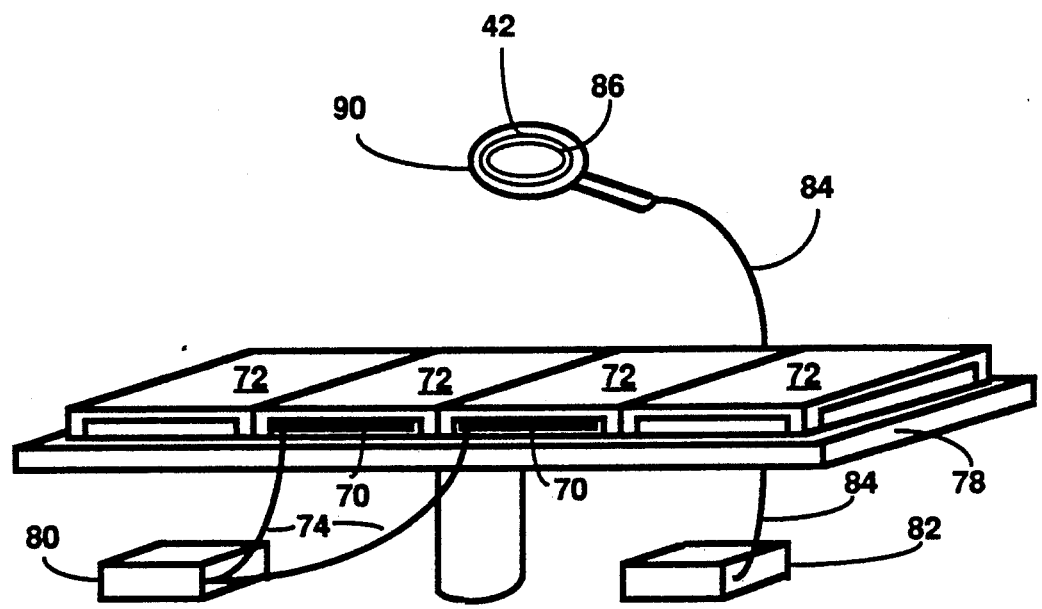
FIGS. 7a and 7b are perspective views of a surgical implement detector installed on an operating table.
Figure 7B:
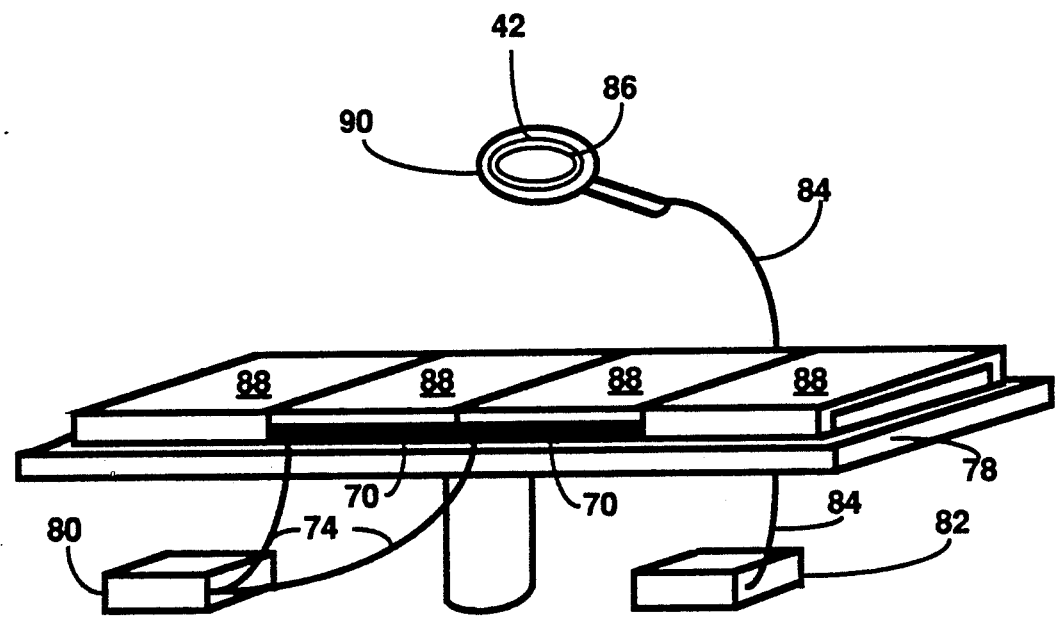

The present invention provides a practical device for detecting surgical implements 20 in a manner so accurate that the problem of post operative retention thereof is virtually eliminated. Specifically, in one embodiment of the invention, shown in FIGS. 6a and 6b, the marker 18 is sewn into a corner 61 of a surgical sponge 63 and attached to forceps 66 by lanyard 68. Referring to FIG. 7a, the transmit antenna 44 is made up of one or more coils 40 imbedded in a panel, 70. The transmit panel 70 is sized to fit in the x-ray film tunnel 72 above the top of surgical table 78. Alternatively, transmit panel 70 is sized to fit in the x-ray film tunnel below the top of surgical table 78. A cable 74 connects the transmit panel 70 to the transmitter electronics 80 attached to the underside of table 78 or located on the floor or wall nearby. Alternatively, as shown in FIG. 7b, the transmitter panels 70 can be placed within padding 88 disposed on top of surgical table 78. The receive coil 42 is housed in a hand-held paddle 90 and passed over the wound by medical personnel before the wound is closed. Receiver electronics 82 is attached by cable 84 to receive paddle 90. Alternatively, the receiver electronics 82 can be battery powered and contained within the hand-held paddle 90. In this manner, the coupling between marker and receiver is optimized. By making the transmitter panel more than one coil and by changing the phase relationship between coils, the transmitted field can be made to rotate, thereby optimizing coupling between transmitted field and marker 18. Alternatively, a single sided antenna can be constructed in which these multiple phase changing transmitting coils are combined with multiple receiving coils in the same antenna panel. Each receive coil 42 is monitored independently. In this way both transmitter 40 to marker 18 and receiver 42 to marker 18 coupling are optimized in a single panel. Enhanced transmitter to marker coupling can be achieved by adding a transmitter coil 86 to the handheld paddle 42. By flipping the paddle over on alternative passes above the wound, the direction of the transmitting field due to its addition to the field generated by panel 70, and therefore its coupling to the marker 18, is markedly changed. As a result, markers 18 having a stationary state within a surgical wound 22 are readily detected in a highly reliable manner.

To illustrate the effectiveness of the surgical implement detector 8 of the present invention, a test was conducted in which the detection rate of randomly oriented stationary markers detected by a conventional magnetomechanical system was compared with that of the implement detector 8 of the invention. During testing, a grid was marked off above the horizontal antenna panel. This grid, measuring 18 inches by 30 inches, consisted of 240 1.5 inch squares. Detection of the markers was measured in each of three orientations ranging from 4" to 26" above the antenna panel. The conventional magnetomechanical detection system evidenced a detection rate of about 75 percent. A paddle containing an 8 inch diameter, 30 turn coil was then passed over the grid and detection was accomplished in accordance with the present invention. The detection rate evidenced by the detector of the invention was 100 percent.

Having thus described the invention in rather full detail, it will be understood that such detail need not be strictly adhered to but that various changes and modifications may suggest themselves to one skilled in the art, all falling within the scope of the invention as defined by the subjoined claims.

What is claimed is:

1. An apparatus for detecting a surgical implement in human or animal tissue, comprising
   (a) means for defining an interrogation zone encompassing a surgical wound in said tissue;
   (b) a marker secured to a surgical implement appointed to be positioned within said wound, said marker comprising a marker element adapted to undergo resonance at only a preselected frequency, causing a substantial change in its effective impedance, when interrogated within a frequency band that is (i) below 1 gigahertz, and (ii) contains a frequency component equal to the preselected frequency, said marker element generating an electromagnetic dipole field that provides said marker element with signal identity;
   (c) interrogating means comprising a frequency generating means, field generating means, and field changing means, said frequency generating means generating said frequency band, said field generating means generating within said interrogation zone an interrogating field having said frequency band, and said field changing means varying the amplitude and direction of said interrogating field to alter the electromagnetic dipole coupling between said marker element and said interrogating field; and
   (d) receiving means comprising a detecting antenna, an antenna changing means, and a detecting means, said detecting antenna receiving said marker dipole field, said antenna changing means varying the orientation and position of said detecting antenna relative to said marker element to alter said electromagnetic dipole coupling therebetween, and said detecting means detecting and verifying said marker dipole field.

2. An apparatus as recited by claim 1, wherein said receiving means further comprises an indicating means for providing an audible or visible alarm when the dipole field of said marker element is detected and verified by said detecting means.

3. An apparatus as recited by claim 1, wherein said marker element comprises a strip of magnetostrictive material adapted to be magnetically biased and thereby armed to mechanically resonate, and to generate said dipole field, at a preselected frequency within the frequency band of said interrogating field, said strip having a magnetomechanical coupling factor, k, greater than zero, where $k^2 = 1 - (f_r/f_a)^2$, $f_r$ and $f_a$ being its resonant and antiresonant frequencies, respectively.

4. An apparatus as recited by claim 1, wherein said marker element comprises a piezoelectric crystal and a coil connected in parallel, said crystal being adapted to mechanically resonate to cause an alternating current to flow within said coil and generate said dipole field at said preselected frequency within the frequency band of said interrogating field.

5. An apparatus as recited by claim 1, wherein said marker element comprises an inductor, resistor, and capacitor circuit adapted to undergo electrical resonance to generate said dipole field at said preselected frequency within the frequency band of said interrogating field.

6. An apparatus as recited by claim 1, wherein said marker element comprises a printed circuit coil adapted to undergo electrical resonance generating said dipole field at said preselected frequency within the frequency band of said interrogating field.

7. An apparatus as recited by claim 1, wherein said field generating means comprises a plurality of loop antennas.

8. An apparatus as recited by claim 7, wherein said field changing means comprises means for varying phase between at least two of said loop antennas.

9. An apparatus as recited by claim 7, wherein said field changing means comprises means for sequentially connecting said loop antennas.

10. An apparatus as recited by claim 1, wherein said field generating means comprises a plurality of electric monopole antennas.

11. An apparatus as recited by claim 1, wherein said field generating means comprises a plurality of electric dipole antennas.

12. An apparatus as recited by claims 1, wherein said field changing means comprises means for displacing said loop antennas.

13. An apparatus as recited by claim 1, wherein said detecting antenna comprises a plurality of loop antennas.

14. An apparatus as recited by claim 13, wherein said antenna changing means comprises means for varying phase between at least two of said plurality of loop antennas.

15. An apparatus as recited by claim 13, wherein said antenna changing means comprises means for sequentially connecting said loop antennas.

16. An apparatus as recited by claim 13, wherein said antenna changing means comprises means for displacing said loop antennas.

17. An apparatus as recited by claim 1, wherein said detecting antenna comprises a plurality of electric monopole antennas.

18. An apparatus as recited by claim 1, wherein said detecting antenna comprises a plurality of electric dipole antennas.

19. An apparatus as recited by claim 1, further comprising a hand-held paddle, said detecting antenna being disposed within said paddle.

20. An apparatus as recited by claim 1, wherein each of said detecting antenna, said field generating means, and said indicating means are disposed within said paddle.

21. An apparatus as recited by claim 1, wherein said field generating means is housed in a panel adapted for mounting within an operating table x-ray film tunnel.

22. An apparatus as recited by claim 1, wherein each of said field generating means and said detecting antenna is housed in a panel adapted for mounting within an operating table x-ray film tunnel.

23. An apparatus as recited by claim 1, wherein said field generating means is housed in a panel adapted to be mounted under padding on an operating table.

24. An apparatus as recited by claim 1, wherein each of said field generating means and said detecting antenna is housed in a panel adapted to be mounted under padding on an operating table.

25. An apparatus as recited by claim 1, wherein said frequency generating means is adapted to provide said field generating means with a burst of single sine wave frequency.

26. An apparatus as recited by claim 1, wherein said frequency generating means is adapted to provide said field generating means with a burst of varying sine wave frequencies.

27. An apparatus as recited by claim 1, wherein said frequency generating means is adapted to provide said field generating means with a pulse, the width of which is less than or equal to $1/(2f)$, where f is the marker element resonant frequency.

28. An apparatus as recited by claim 1, wherein said detecting means is adapted to detect and verify said dipole field of said marker element by phase difference with said interrogating field.

29. An apparatus as recited by claim 1, wherein said detecting means is adapted to detect and verify phase difference between said dipole field of said marker element and said interrogating field.

30. An apparatus as recited by claim 1, wherein said detecting means is adapted to detect and verify ring down of said dipole field of said marker element upon termination of said interrogating field.

31. A method for detecting a surgical implement in human or animal tissue, comprising the steps of:
(a) defining an interrogation zone encompassing a surgical wound in said tissue;
(b) attaching a marker to said surgical implement, said surgical implement being appointed for disposition within said wound, the marker comprising a marker element adapted to undergo resonance at only a preselected frequency, causing a substantial change in its effective impedance, when interrogated within a frequency band that is (i) below 1 gigahertz and (ii) contains a frequency component equal to the preselected frequency, and to generate an electromagnetic dipole field providing the marker with signal identity;
(c) interrogating said zone by (i) generating therewithin said frequency band and an interrogating field having said frequency band and (ii) varying amplitude and direction of said interrogating field to alter electromagnetic dipole coupling between said marker and said interrogating field; and
(d) receiving said dipole field by varying orientation and position of a detecting antenna relative to said marker to alter said electromagnetic dipole coupling therebetween and assure detection of said implement.

* * * * *